United States Patent
Cheng (10) Patent No.: US 9,820,872 B2
(45) Date of Patent: Nov. 21, 2017

(54) STRUCTURE OF CONNECTION AND ADJUSTMENT ASSEMBLY OF SUPPORT SOCKET JOINT OF PROSTHESIS

(71) Applicant: KEN DALL ENTERPRISE CO., LTD., New Taipei (TW)

(72) Inventor: Chia-Pao Cheng, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 13 days.

(21) Appl. No.: 14/958,909

(22) Filed: Dec. 3, 2015

(65) Prior Publication Data

US 2017/0156897 A1 Jun. 8, 2017

(51) Int. Cl.
*A61F 2/80* (2006.01)
*F16H 19/04* (2006.01)
*A61F 2/50* (2006.01)

(52) U.S. Cl.
CPC .............. *A61F 2/80* (2013.01); *F16H 19/04* (2013.01); *A61F 2002/5016* (2013.01); *A61F 2002/5038* (2013.01); *F16H 2019/046* (2013.01)

(58) Field of Classification Search
CPC ........................... A61F 2/80; A61F 2002/5016
See application file for complete search history.

(56) References Cited

U.S. PATENT DOCUMENTS

| | | | | |
|---|---|---|---|---|
| 7,429,271 B2 * | 9/2008 | Mosler | ...................... | A61F 2/76 192/223.2 |
| 8,435,308 B2 * | 5/2013 | Atteraas | .................... | A61F 2/76 623/32 |
| 8,623,092 B2 * | 1/2014 | Bickley | ..................... | A61F 2/40 623/18.11 |
| 2005/0216096 A1 * | 9/2005 | Wagman | ................... | A61F 2/78 623/38 |
| 2005/0244220 A1 * | 11/2005 | Ingimarsson | ............. | A61F 2/60 403/344 |

* cited by examiner

*Primary Examiner* — Bruce E Snow
*Assistant Examiner* — Melissa Hoban
(74) *Attorney, Agent, or Firm* — Leong C. Lei (57) ABSTRACT

An improved structure of a connection and adjustment assembly of a support socket joint of a prosthesis includes a connector, in which a vertical through hole and a horizontal through hole are formed. A support socket is provided on the connector and receives therein an arrest axle extending through the vertical through hole. The horizontal through hole receives therein a shaft, which has an end having a toothed wheel engageable with the arrest axle and an opposite end to which a second one-way bearing, a sleeve, and a knob cap are mounted. The knob cap has an interior that is an elliptical configuration corresponding to and mating an outside elliptical configuration of the sleeve. Pressing a knob causes movement of the sleeve and thus components mounted to the shaft so as to have the toothed wheel disengage from the arrest axle, allowing the arrest axle to be withdrawn out.

3 Claims, 8 Drawing Sheets

STRUCTURE OF CONNECTION AND ADJUSTMENT ASSEMBLY OF SUPPORT SOCKET JOINT OF PROSTHESIS

(a) TECHNICAL FIELD OF THE INVENTION

The present invention relates to an improved structure of a connection and adjustment assembly of a support socket joint of a prosthesis, which comprises a sleeve having an elliptical outside configuration mating a knob cap corresponding in shape to and receiving the sleeve to fit therein and a shaft extending through the sleeve and a knob is operable to cause the sleeve to make a displacement for disengaging toothed wheel from a mating arrest axle, together with the arrangement of a first one-way bearing and a second one-way bearing, to allow for safe adjustment of the arrest axle.

(b) DESCRIPTION OF THE PRIOR ART

U.S. Pat. No. 7,429,271 discloses a clamping freewheel mechanism and a use thereof for a prosthetic part, which is applied to lock a prosthetic part under a linear movement. The clamping freewheel mechanism is mounted to a housing and comprises a shaft that is formed by an inner member that is connected to a transmission element received in a hollow member. The shaft is axially movably received in a sleeve having rolling elements therein. The sleeve is arranged in the housing. An opposite end of the housing is provided with an operation member, a spring, and a head member connected to the inner member.

The primary purpose of the clamping freewheel mechanism is to separate the two functions of fixing and axially moving a stop pin. Thus, without pressing the operation member, the inner member of the transmission member and the hollow shaft are constrained by the rotation of the rolling elements so that the stop pin can only be inserted into a guide hole to engage the transmission member and cannot be withdrawn. When the operation member is pressed down, the inner member and the transmission member are driven to release the engagement between the stop pin and the transmission member.

However, the way of separation of the stop pin and the transmission member, although effective in achieving the function of fixing and separation, requires a complicated mechanism so that the manufacturing process is difficult and the manufacturing cost is excessively high.

Thus, in view of the above problems, the present invention aims to provide an improved structure of a connection and adjustment assembly of a support socket joint of a prosthesis that involves a simplified mechanism, is easy to adjust, and improve operation safety.

SUMMARY OF THE INVENTION

An object of the present invention is to allow for displacement of a shaft inside a connector for disengaging a toothed wheel from a corresponding arrest axle and to provide a sleeve having an elliptic configuration and a first one-way bearing and a second one-way bearing to achieve adjustment of the arrest axle in a safe manner and to overcome the expensive installation cost of the prior art mechanism.

The present invention provides a support socket joint connection and adjustment assembly of a prosthesis, which comprises a support socket, in which an arrest axle is arranged. The arrest axle comprises a plurality of circumferential grooves formed thereon in an equally spaced manner. A connector comprises a vertical through hole and a horizontal through hole formed therein and partly intersecting each other. The vertical through hole receives the arrest axle to extend therethrough. The horizontal through hole receives a shaft to extend therein. The shaft has an end section that comprises a toothed wheel and a first one-way bearing mounted thereto. The toothed wheel is fit outside the first one-way bearing in such a way that the toothed wheel is engageable with and thus operatively coupled to the arrest axle. The shaft has an opposite end section to which a second one-way bearing, a sleeve, and a knob cap are sequentially mounted. The knob cap comprises a spring arranged therein to resiliently support a knob.

The present invention provides a second one-way bearing that has a circular outside configuration corresponding to and securely fit in the sleeve and provides the sleeve with an outside configuration that is elliptical to allow the sleeve to be fit in the interior of the knob cap that corresponds in shape thereto. With a knob pressed down, the sleeve and the components mounted to said one end of the shaft are caused to move by a predetermined distance thereby making the toothed wheel move and thus disengage from the arrest axle, allowing the arrest axle to be withdrawn out for adjustment. When the toothed wheel returns, the arrest axle also returns to engage with the toothed wheel to establish constraint therebetween, allowing the arrest axle to move in a given direction to achieve vertical one-way adjustment. The entire mechanism is simple and safe and the manufacturing cost is reduced, allowing a user to use in a safe and affordable manner.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

A preferred embodiment accordant to the present invention will be described, with reference to the attached drawings, for better understanding of the present invention. The present invention provides an improved structure of a connection and adjustment assembly of a support socket joint of a prosthesis, which comprises, as shown in FIGS. 1-8, a support socket (1) that is provided for receiving a remaining portion of a damaged limb of a user to be positioned on and coupled to a top end thereof. The support socket (1) comprises an arrest axle (11) arranged in the interior thereof. The arrest axle (11) comprises a plurality of circumferential grooves (12) formed thereon in an equally-spaced manner. Also included is a connector (2) in which a vertical through hole (21) and a horizontal through hole (22) are defined and partly intersect each other. The vertical through hole (21) receives the arrest axle (11) to extend therethrough. The horizontal through hole (22) receives a shaft (3) to extend therein and the horizontal through hole (22) is formed to provide a gap (23) therein. The shaft (3) has an end section on which a first one-way bearing (31) and a toothed wheel (32) are mounted by receiving the shaft to extend therethrough. Respectively arranged on opposite sides of the first one-way bearing (31) are bearing washers (33) that prevent undesired separation of the toothed wheel (32) and the shaft (3). The toothed wheel (32) is securely fit outside the first one-way bearing (31) in such a way that the toothed wheel (32) operatively corresponds to and is engageable with the circumferential grooves of the arrest axle (11). The shaft (3) has an opposite end section to which a second one-way bearing (34), a sleeve (35), and a knob cap (36) are sequentially mounted by receiving the shaft to extend therethrough. Arranged inside the knob cap (36) is a spring (37) that resiliently supports and biases a knob (38).

Figure 1:
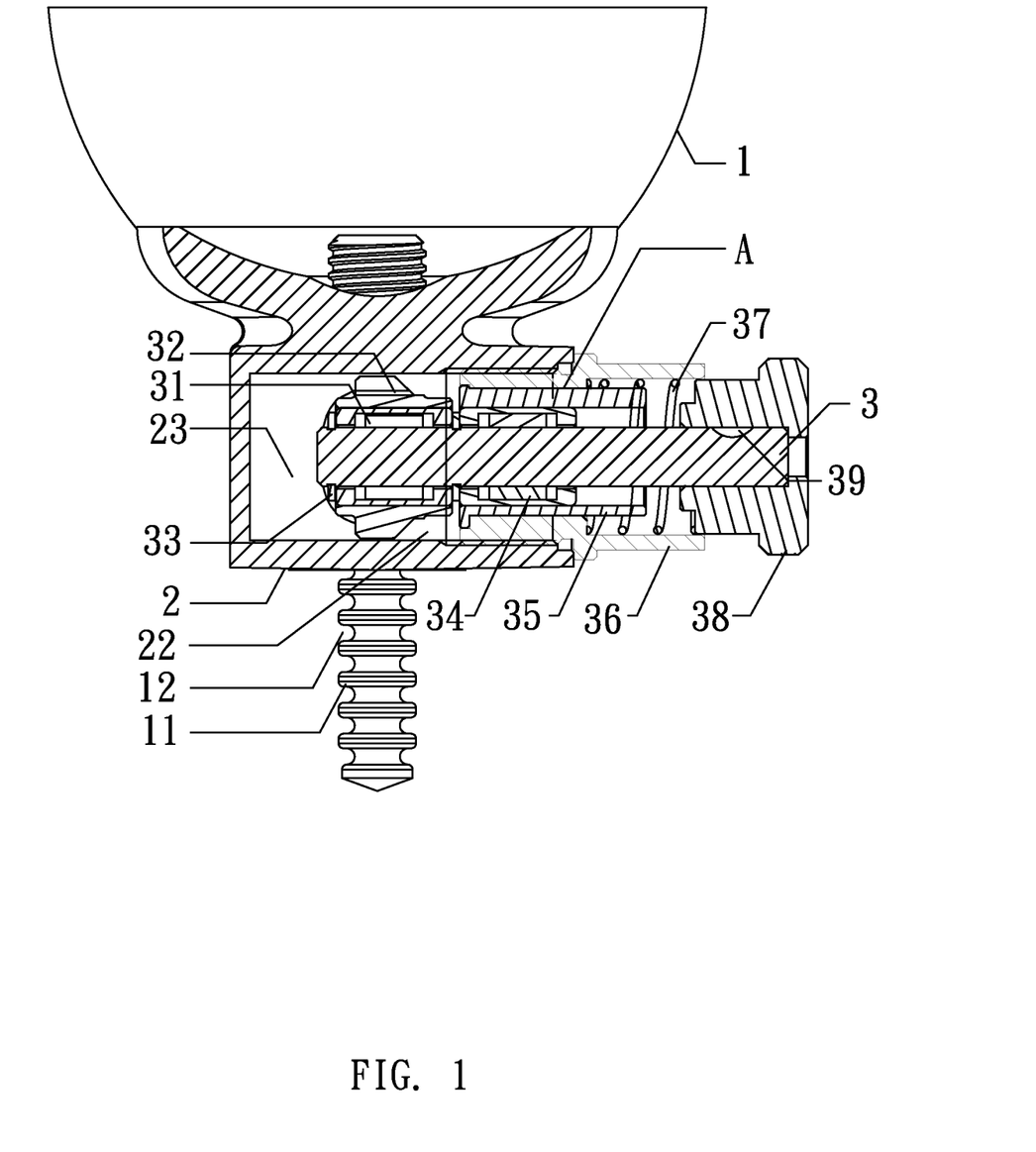
FIG. 1 is a perspective view of the present invention.
Figure 2:
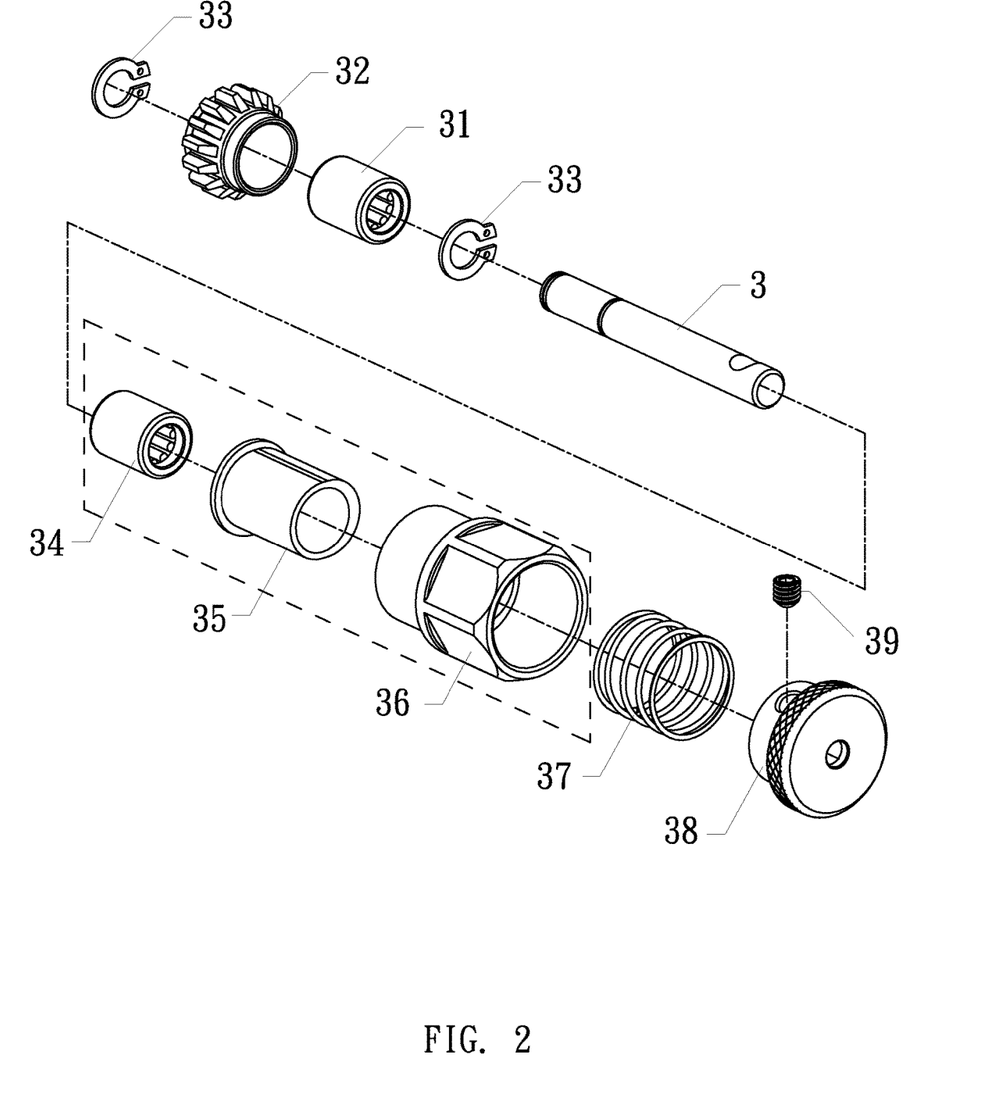
FIG. 2 is an exploded view of the preferred embodiment.
Figure 3:
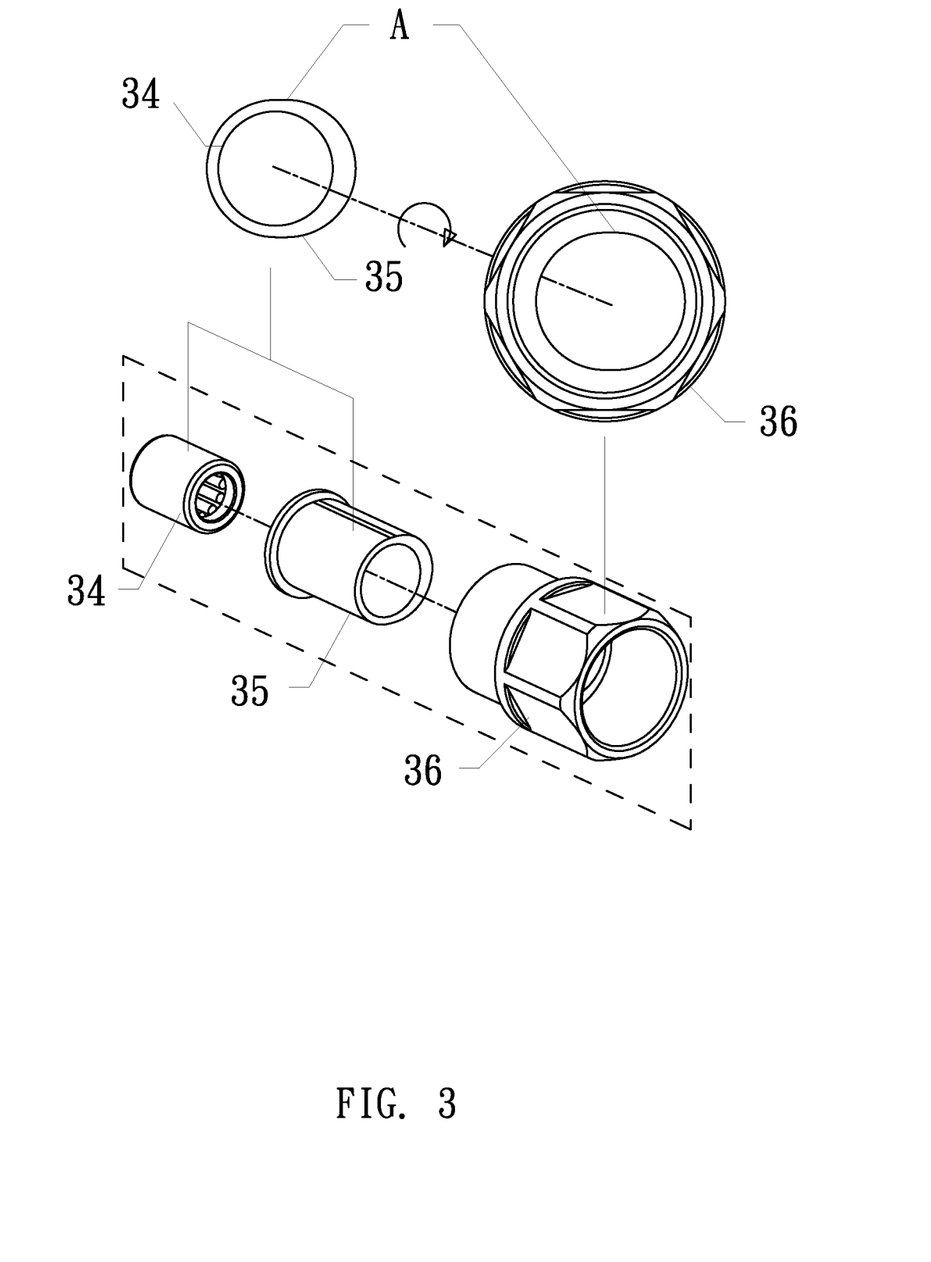
FIG. 3 is a schematic view showing components of the present invention.

Referring to FIGS. 1-3, said opposite end section of the shaft (3) is provided with an aperture formed in an outer circumference thereof. The aperture and a circumference of the knob (38) corresponding thereto are coupled together by a positioning element (39) so that the knob (38) that is moveable through depression drives the shaft (3), together with components mounted thereto, to move. As shown in the drawings, the second one-way bearing (34) has inside and outside configurations that are both circular. The inside configuration is provided for positioning the shaft (3), while the outside configuration of the second one-way bearing (34) is made corresponding to an interior of the sleeve (35) that has a circular configuration to allow the two securely fit to and fixed to each other so that when the shaft (3), due to an elliptical configuration of the knob cap (36), the second one-way bearing (34) and the sleeve (35) are allowed for linear movement only and the shaft (3) is constrained by the second one-way bearing (34) to do motion in one single direction. The sleeve (35) has an outside configuration that is elliptical and mates an elliptical configuration (A) of the interior of the knob cap (36) so that the arrangement between the outside of the sleeve (35) and the inside of the knob cap (36) provides means for adjustment. When the shaft (3) is received and set in the horizontal through hole (22), the first one-way bearing (31) and the second one-way bearing (34) are both arranged for rotation in the same direction, such as clockwise direction. Thus, when the sleeve (35) is not acted upon by an external force and thus is not moved, the elliptical configuration allows for being securely held in the horizontal through hole (22) without being influenced by the shaft (3) to rotate thereby enhancing safety of the entire mechanism.

Figure 4:
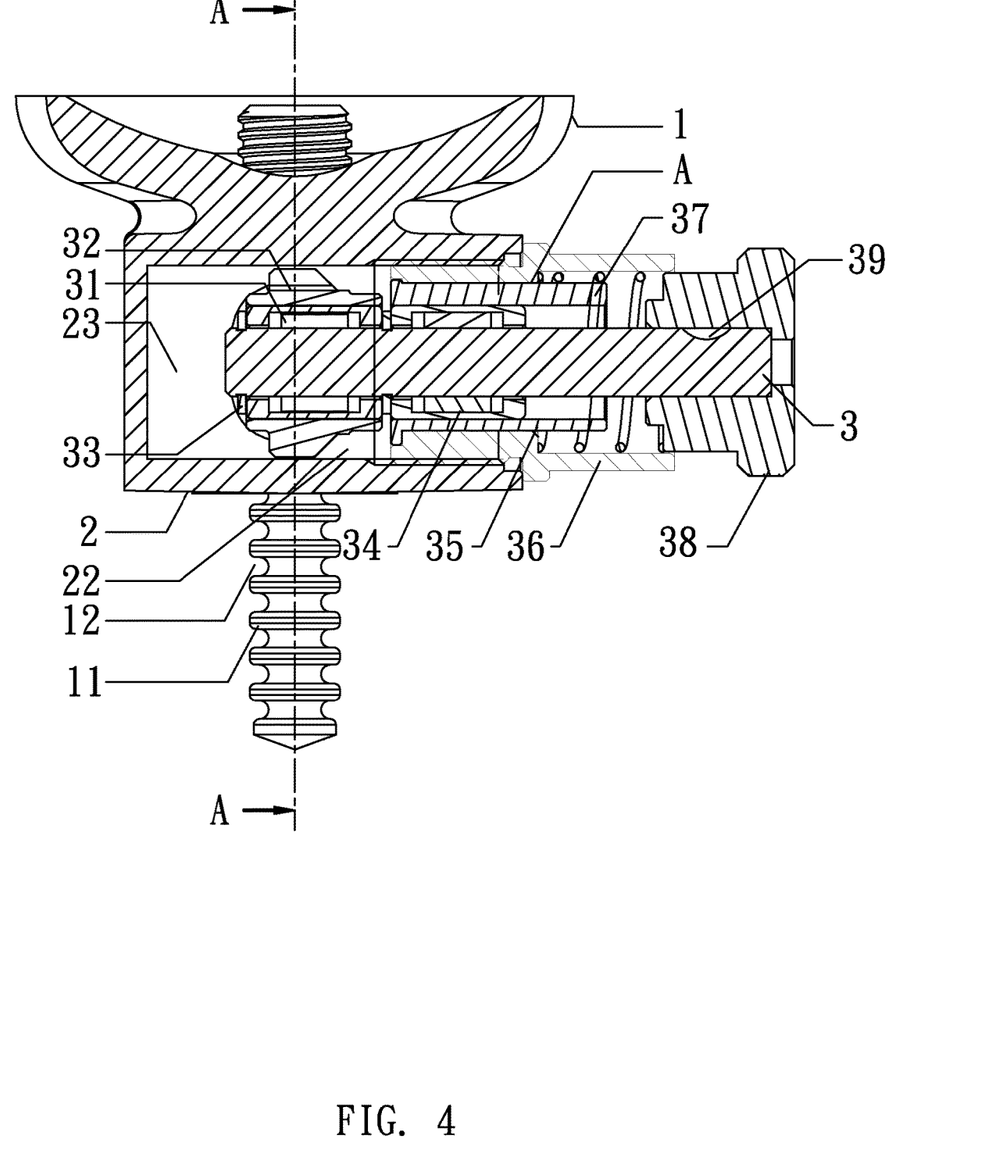
FIG. 4 is a cross-sectional view illustrating movement of an arrest axle of the present invention in a vertical one-way manner.
Figure 5:
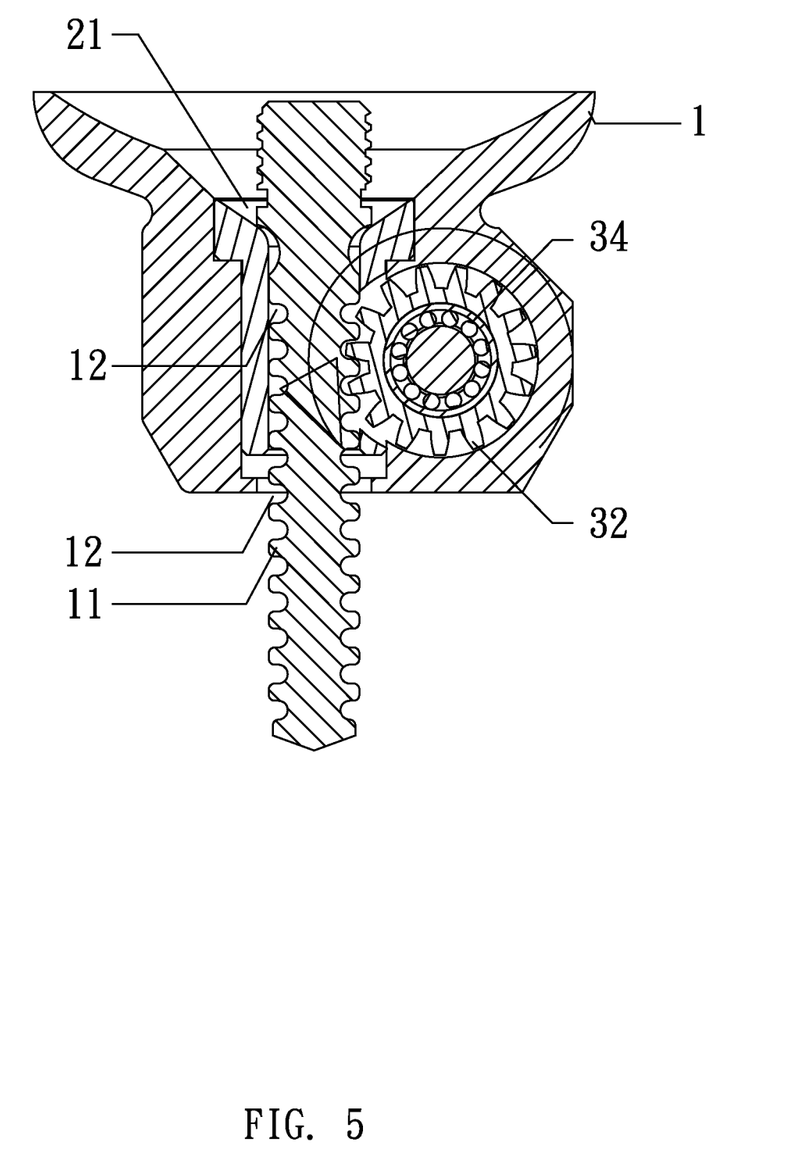
FIG. 5 is a cross-sectional view taken along line A-A, illustrating the movement of the arrest axle of the present invention in a vertical one-way manner.
Figure 6:
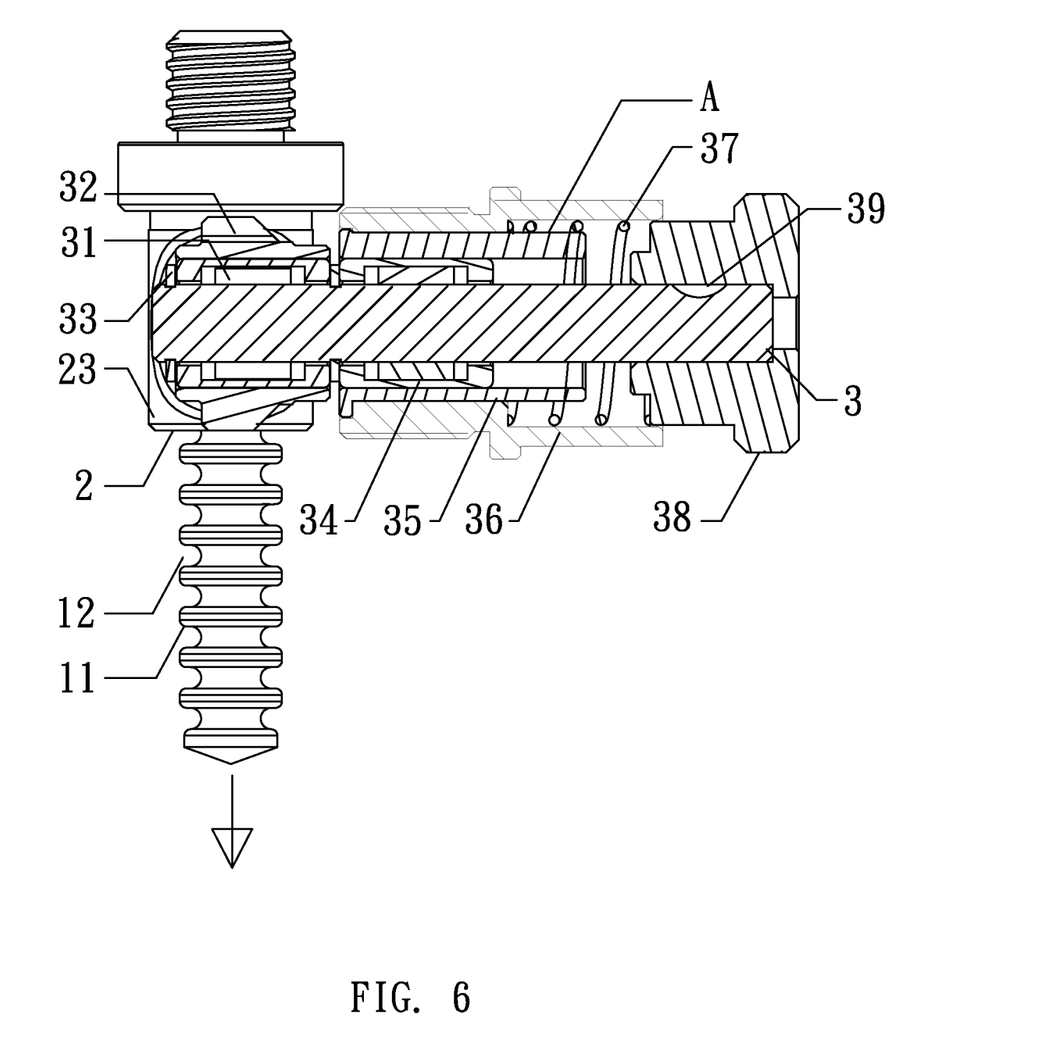
FIG. 6 is a schematic view showing a portion of the present invention to illustrate the vertical one-way movement.

Referring to FIGS. 4-6, when the knob (38) is not acted upon and thus pressed down by an external force to displace, it can be seen that with the knob (38) being not pressed down, the arrest axle (11) is constrained due to the second one-way bearing (34) contained in the sleeve (35) is still located in the elliptical inside configuration of the knob cap (36) so that components that are mounted on the shaft (3) are prevented from rotation, and the toothed wheel (32) is in engagement with the arrest axle (11), whereby under such a condition, the arrest axle (11) is only allowed to move downward to comply with the allowable rotation of the first one-way bearing (31) and the second one-way bearing (34) in a given direction for achieving vertical one-way adjustment.

Figure 7:
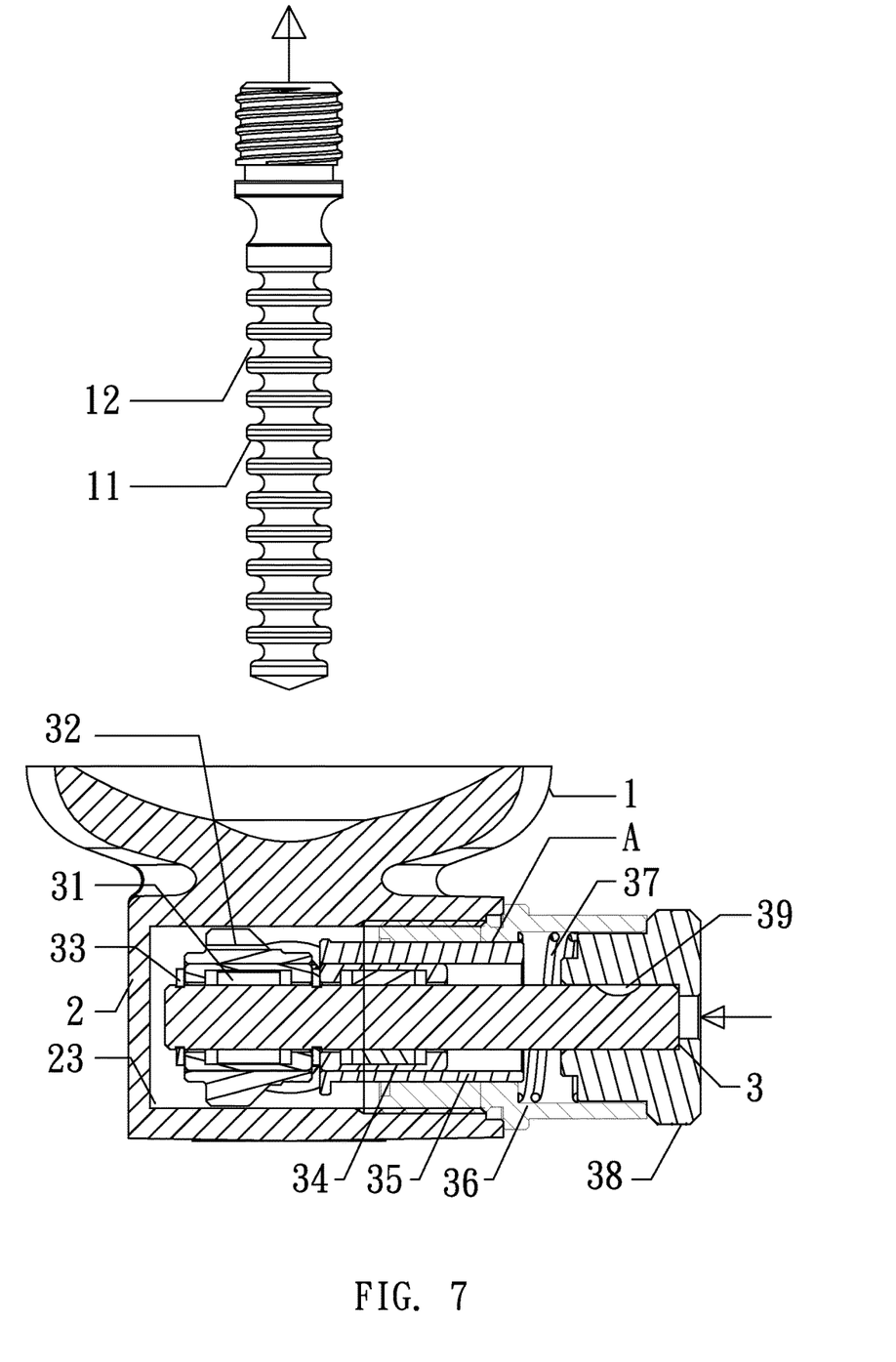
FIG. 7 is a cross-sectional view illustrating the arrest axle movable in dual directions.
Figure 8:
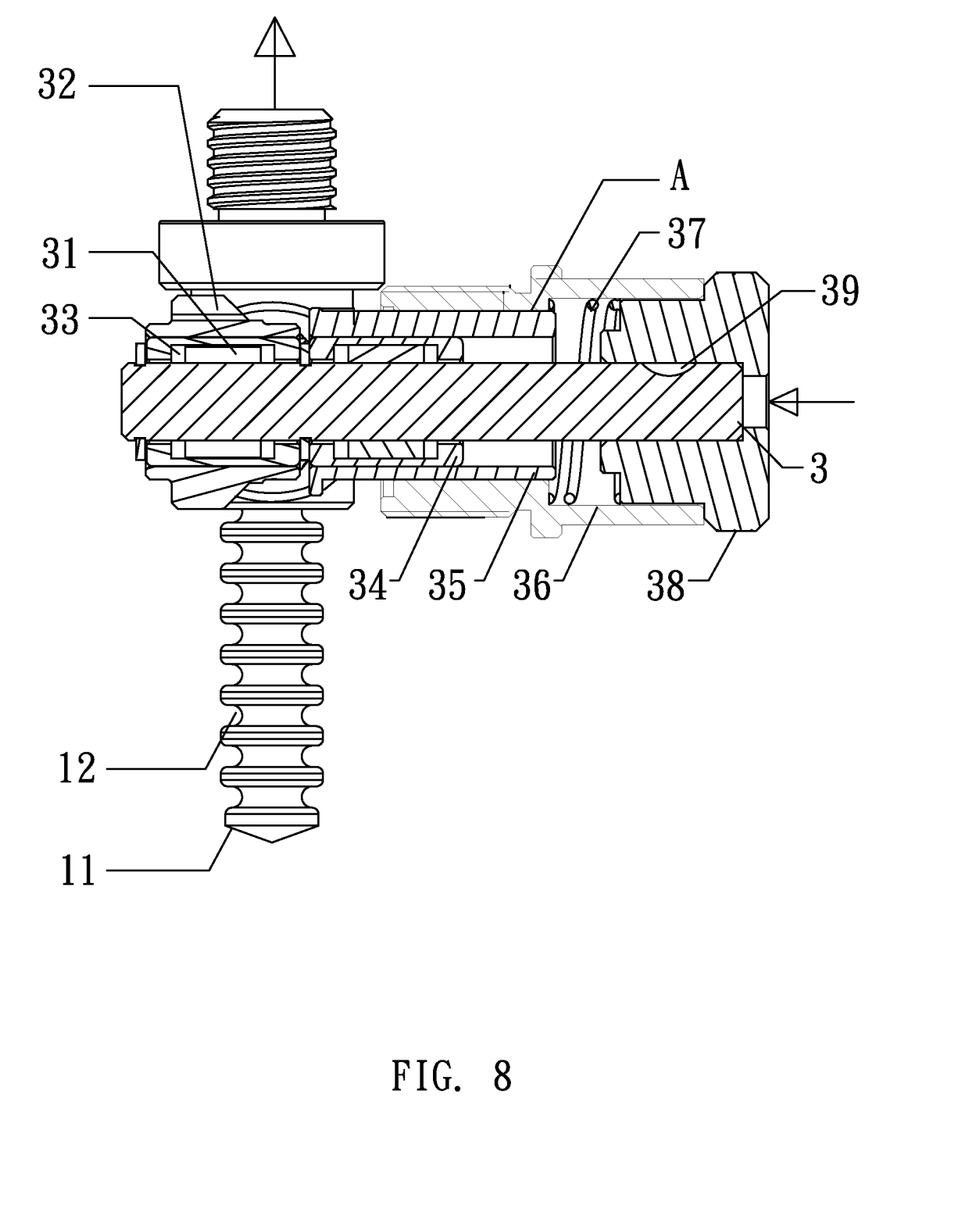
FIG. 8 is a schematic view showing a portion of the present invention to illustrate vertical two-way movement.

Referring to FIGS. 7-8, when the knob (38) is acted upon and pressed down by an external force to displace and thus drives the sleeve (35) to move, the second one-way bearing (34) and the toothed wheel (32) are also moved so that under such a condition, the toothed wheel (32) is moved into the gap (23) and thus disengages from the arrest axle (11), allowing the arrest axle (11) to be withdrawn out for re-adjustment to achieve the most comfortable position for the user.

In summary, the present invention provides an improved structure of a connection and adjustment assembly of a support socket joint of a prosthesis, in which a second one-way bearing (34) is received and mounted in a sleeve (35) and the sleeve (35) is received in a knob cap (36), wherein the sleeve (35) has an elliptical outside configuration that mates and is fit into an interior of the knob cap (36) having a corresponding configuration. By pressing down a knob (38) to deform a spring (37) and moves the sleeve (35), components mounted to an end of a shaft (3) are moved so that with the sleeve (35) being moved by a predetermined distance, a toothed wheel (32) and an arrest axle (11) are released from engagement with each other or reversely re-engage with each other. The entire mechanism is made simple and protection means is provided for better safety so that a user may make adjustment easily.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A support socket joint connection and adjustment assembly of a prosthesis, comprising a support socket, in which an arrest axle is arranged, the arrest axle comprising a plurality of circumferential grooves formed thereon in an equally spaced manner; a connector comprising a vertical through hole and a horizontal through hole formed therein and partly intersecting each other, the vertical through hole receiving the arrest axle to extend therethrough, the horizontal through hole receiving a shaft to extend therein, the shaft having an end section that comprises a toothed wheel and a first one-way bearing mounted thereto, the toothed wheel being fit outside the first one-way bearing in such a way that the toothed wheel is engageable with and thus operatively coupled to the arrest axle, the shaft having an opposite end section to which a second one-way bearing, a sleeve, and a knob cap are sequentially mounted, the knob cap comprising a spring arranged therein to resiliently support a knob, characterized in that:

the sleeve has an outside configuration that is elliptical and is fit in an interior of knob cap that has a configuration corresponding thereto, the sleeve having an inside configuration that is circular to receive the second one-way bearing to fit therein so that when a knob is pressed to cause the sleeve to displace by a predetermined distance to have components mounted to said one end section of the shaft moved, making the toothed wheel disengage from the arrest axle, whereby the arrest axle is withdrawable for adjustment; and when the sleeve returns, the toothed wheel also returns back to engage with the arrest axle, making the arrest axle constrained for adjustment;

wherein the toothed wheel is fit outside the first one-way bearing that is mounted to the end section of the shaft such that the toothed wheel is rotatable with respect to the shaft by means of the first one-way bearing and wherein the elliptical outside configuration of the sleeve and the corresponding interior configuration of the knob cap collectively define an engagement therebetween that allows the sleeve and the second one-way bearing received in the sleeve to be linearly movable with respect to the knob cap while making the sleeve and the second one-way bearing received in the sleeve rotatably fixed to the knob cap.

2. The support socket joint connection and adjustment assembly according to claim 1, wherein the horizontal through hole further comprises a gap, which is provided at a predetermined position of the horizontal through hole to allow the toothed wheel to move into such a gap for disengagement from the arrest axle.

3. The support socket joint connection and adjustment assembly according to claim 1, wherein the first one-way bearing and the second one-way bearing are arranged for rotation in the same direction.

\* \* \* \* \*